United States Patent [19]

Ulick et al.

[11] Patent Number: 5,070,109

[45] Date of Patent: Dec. 3, 1991

[54] RECOVERY OF HYDROCRABON PRODUCTS FROM ELASTOMERS

[75] Inventors: Thomas J. Ulick, Barrington; William E. Carner, Round Lake Beach, both of Ill.

[73] Assignee: Rubber Waste, Inc., Zion, Ill.

[21] Appl. No.: 453,711

[22] Filed: Dec. 20, 1989

[51] Int. Cl.$^5$ .................... C08J 11/04; C08J 11/20; C08L 95/00

[52] U.S. Cl. .................... 521/41; 521/49.5; 521/45.5; 585/241; 524/71; 524/62

[58] Field of Search .................... 521/41, 44, 45.5, 62, 521/71; 585/241

[56] References Cited

U.S. PATENT DOCUMENTS

| | | | |
|---|---|---|---|
| 2,311,301 | 2/1943 | Livermore | 524/64 |
| 2,347,211 | 5/1944 | Merrill et al. | 524/64 |
| 2,578,001 | 5/1949 | Cubberley et al. | 524/68 |
| 4,030,984 | 6/1977 | Chambers | 521/45.5 |
| 4,108,730 | 8/1978 | Chen et al. | 585/241 |
| 4,430,464 | 2/1984 | Oliver | 524/59 |
| 4,506,034 | 3/1985 | Munih | 521/45.5 |
| 4,588,634 | 5/1986 | Pagen et al. | 428/283 |
| 4,609,696 | 9/1986 | Wilkes | 524/59 |
| 4,647,443 | 3/1987 | Apffel | 585/241 |
| 4,665,101 | 5/1987 | Ficker | 521/45.5 |

*Primary Examiner*—Allan M. Lieberman
*Attorney, Agent, or Firm*—Welsh & Katz, Ltd.

[57] ABSTRACT

A method is disclosed for the recovery of hydrocarbon products from elastomeric products such as discarded vehicle tires and other rubber products. The elastomeric products are immersed in a liquid heat transfer medium and heated to a temperature in the range of from about 575° F. to about 600° F. for a period of from about 0.5 to about 2.0 hours. The process produces a methane-containing gas product, a low boiling fuel oil fraction, a light fraction elastomeric hydrocarbon solid, a heavy fraction elastomeric hydrocarbon solid, and steel cord when steel belted radial tires are processed.

46 Claims, 1 Drawing Sheet

RECOVERY OF HYDROCRABON PRODUCTS FROM ELASTOMERS

BACKGROUND OF THE INVENTION

The present invention relates to a method for the recovery of hydrocarbon products from elastomeric products. More particularly, the present invention relates to a method for the recovery of various hydrocarbon products from elastomeric products such as discarded vehicle tires and other rubber products. In particular, the present invention relates to a method for the recovery of various hydrocarbon products, including elastomeric hydrocarbons, and miscellaneous scrap metals from discarded rubber and other elastomeric products such as discarded vehicle tires, hoses, gaskets, coated electrical wire, and the like.

As used herein, the terms "elastomer", "elastomeric", and the like refer to natural rubber, synthetic rubber, and other polymers that can be stretched at room temperature to at least twice their original length and, after having been stretched, will return to approximately their original length in a short time when the stress is removed. In general, elastomers also are "resilient" in that they have the ability to recover their size and shape following deformation, such as by a tensile or compressive force.

It is well known that vehicle tires and certain other elastomeric products do not compact well and are not degradable in landfills. It is further known that, while shredding may reduce the volume of such products in landfills, such products still occupy a significant proportion of total landfill volume. Many landfill operators refuse to accept whole tires or are prohibited by law from accepting whole tires for placement in their landfills. It is estimated that hundreds of millions of discarded vehicle tires are dumped illegally or are stored throughout the nation, and millions more are accumulating annually. Many public agencies are becoming increasingly concerned about the public health hazards associated with the breeding of certain mosquito strains in discarded rubber tires, and laws have been enacted which regulate or prohibit the storage of discarded tires. In addition, discarded tires and other elastomeric products represent an enormous untapped and wasted hydrocarbon resource. However, at present there is seemingly no viable economically or environmentally sound process available to dispose of the enormous accumulation of discarded tires, or to recover the hydrocarbon resources contained in discarded tires and other discarded elastomeric products.

Accordingly, it is an object of the present invention to provide a method for the disposal of discarded rubber tires and for the recovery of the hydrocarbon and other resources contained therein.

It is another object of the present invention to provide a method for the disposal of other discarded elastomeric products such as discarded hoses, gaskets, elastomeric coated electrical wire, and any other discarded elastomers of rubber or plastic.

It is a further object of the present invention to provide a method for the conversion of whole or shredded discarded tires and other discarded elastomeric products into useful hydrocarbon products and clean scrap metal when such metal is present in the feed stock.

It is a still further object of the present invention to provide a method for converting discarded elastomeric products into elastomeric hydrocarbons which are suitable for use in making roofing materials, waterproofing sealants, binders and other useful products.

It is yet another object of the present invention to provide a method for the disposal of discarded rubber vehicle tires and other discarded elastomeric products, and for the conversion of such tires and other elastomeric products into various hydrocarbon products and scrap metal in an environmentally safe manner.

These and other objects of the present invention, as well as the advantages thereof, will become more clear from the disclosure which follows.

SUMMARY OF THE INVENTION

By the practice of the present invention, discarded rubber vehicle tires and other discarded elastomeric products may be converted into five useful products. The first product is a light fraction elastomeric hydrocarbon solid and the second product is a heavy fraction elastomeric hydrocarbon solid. In addition, the process of the present invention produces a methane-containing gas fraction as the third product and a light hydrocarbon liquid fraction, such as a fuel oil fraction, as the fourth product. The final product comprises clean scrap metal, such as segments of steel cords from the fabric of the discarded vehicle tires.

The light fraction elastomeric hydrocarbon solid and the heavy fraction elastomeric hydrocarbon solid may each contain small quantities of fiberglass fibers from belting and reinforcement in discarded tires and some other rubber and elastomeric products. The fiberglass fibers do not interfere with the use of the light fraction elastomeric hydrocarbon solid and the heavy fraction elastomeric hydrocarbon solid for the purposes stated hereinabove, and, in fact, in many instances the fibers provide additional mechanical strength and reinforcement to the end products, such as a roofing composition. The methane-containing gas fraction and the light hydrocarbon liquid fraction are both suitable for use as fuels.

In one aspect, the method of this invention provides for the recovery of hydrocarbons from elastomeric products, such as discarded vehicle tires and other rubber products. The elastomeric products are passed into a substantially air-free thermal processing zone. A low volatility, high molecular weight, highly aromatic hydrocarbon liquid contacts the elastomeric products in the thermal processing zone. Preferably, the elastomeric products are kept immersed in this low volatility hydrocarbon liquid, which acts as a heat transfer medium. The thermal processing zone is maintained under elevated temperature conditions sufficient to generate a first hydrocarbon vapor from the elastomeric products which are immersed in the hydrocarbon heat transfer medium within the processing zone. This first hydrocarbon vapor is passed from the thermal processing zone into a condensation zone wherein it is separated into a second hydrocarbon vapor containing methane and light hydrocarbon vapors, and into a light fraction first hydrocarbon liquid which may be utilized as a fuel oil. A light fraction elastomeric first hydrocarbon solid and a heavy fraction elastomeric second hydrocarbon solid are recovered from the processing zone as separate products.

In one embodiment of the foregoing method, a heavy fraction second hydrocarbon liquid is withdrawn from the processing zone at an elevated temperature. This second hydrocarbon liquid contains a portion of the second hydrocarbon solid, which settles out of the second hydrocarbon liquid to produce a separated third hydrocarbon liquid. The third hydrocarbon liquid is then cooled after the separation step to provide the first hydrocarbon solid.

In a another embodiment of the foregoing method, the elastomeric products which are charged to the thermal processing zone may comprise vehicle tires, and steel cord will be recovered from the processing zone. Upon removal from the processing zone, the steel cord will be found to be coated with an amorphous third hydrocarbon solid. The third hydrocarbon solid is cleaned from the steel cord by a cleaning liquid to provide a substantially hydrocarbon-free steel cord product and a mixture of the third hydrocarbon solid in the cleaning liquid. The third hydrocarbon solid is settled out from the cleaning liquid, and the cleaning liquid may then be recycled for further washing of steel cord product. The third hydrocarbon solid is then combined with the recovered second hydrocarbon solid. In a further preferred embodiment, the cleaning liquid is a portion of the first hydrocarbon liquid, which is typically a fuel oil.

In a further embodiment of the foregoing method, the light fraction elastomeric first hydrocarbon solid and the heavy fraction elastomeric second hydrocarbon solid are not recovered from the processing zone as separate products. Instead, a heavy fraction second hydrocarbon liquid comprising thermally cracked elastomeric hydrocarbons and heat transfer medium is withdrawn from this thermal processing zone. This second hydrocarbon liquid is cooled to provide a recovered elastomeric solid product comprising the thermally cracked elastomeric hydrocarbons and the heat transfer medium. Thus, both fractions of thermally cracked elastomeric hydrocarbons are contained in a single solid which also includes the heat transfer medium.

In a still further embodiment of the foregoing method, the products which are charged to the thermal processing zone may be polymeric products which are not elastomeric and resilient. Since the elastomeric products which have been mentioned with particularity are in themselves polymers, those skilled in the art can understand that the foregoing methods have equal application to any polymeric material which need not be elastomeric. Such non-elastomeric polymeric materials may be flexible films or rigid articles, and they include any of the well known plastics such as polyethylene and polypropylene.

A clearer understanding of the present invention will be obtained from the disclosure which follows when read in light of the accompanying drawing.

DESCRIPTION OF PREFERRED EMBODIMENTS

Figure 1:
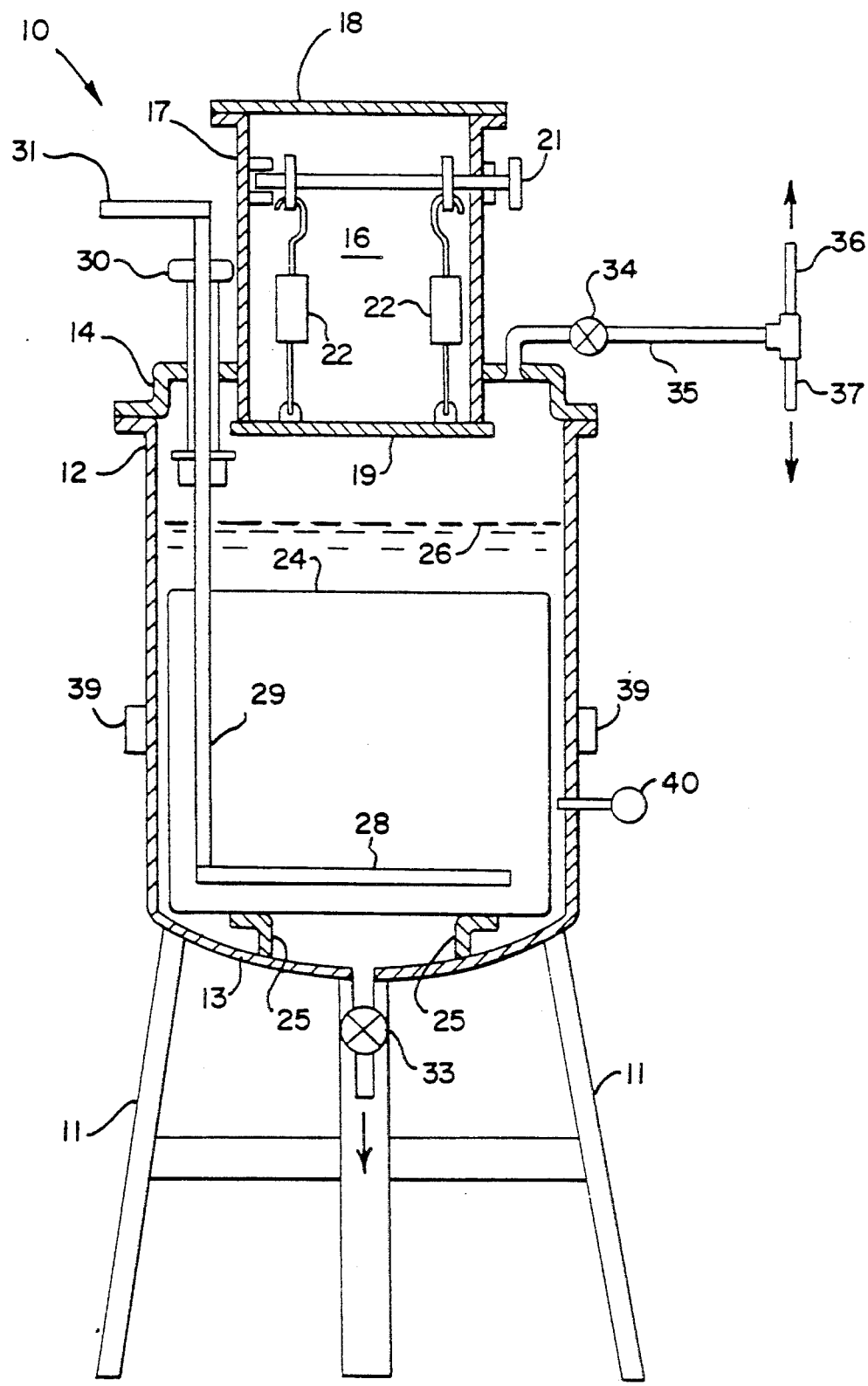
FIG. 1 is a simplified schematic representation of a batch reactor vessel which may be utilized in the practice of the method of the present invention.

The method of the present invention has been tested by means of a batch process. However, those skilled in the art can readily ascertain how to adapt the method of this invention for a continuous operation.

The batch process utilizes a large metal vessel with various inlet and outlet openings in the top and the bottom which are gas and liquid tight. The vessel must be capable of being heated to a temperature in the range of from at least about 575° F. to about 600° F. and of being maintained in this temperature range when rubber tires are being processed. Other rubber products may require a different temperature level. Any type of heating means may be utilized, including an external jacket on the vessel for the circulation of a high temperature heating liquid. Preferably, electrical heaters may be used, either as band heaters on the outside surface of the vessel or as immersion heaters within the liquid in the vessel. The tires or cut up tire pieces which are added to the vessel must be submerged in the hydrocarbon heat transfer medium. Preferably the vessel contents are agitated. This may be undertaken by means of a paddle mixer within the vessel. Alternatively, the agitation of the liquid heat transfer medium and the heating of the vessel may be undertaken by pumping the heat transfer medium from the lower region of the vessel, passing it through a high temperature heat exchanger to pick up heat, and then returning it to the upper region of the vessel.

The vapor which is generated by the process of this invention is removed from the top of the vessel and sent to a condensation means. A fuel oil liquid fraction (a light fraction of hydrocarbons containing more than five carbon atoms per molecule) is condensed from this vapor and it may be sent to storage. The remaining noncondensed vapor contains methane, but it may also typically contain hydrocarbon vapor having from two to five carbon atoms per molecule. This methane-containing vapor is removed from the condensation zone and it may be compressed and stored. Alternatively, the fuel oil product and the methane-containing gas product may be burned in a furnace in order to pass at least a portion of the generated thermal energy into the thermal processing zone (the batch vessel). Additionally, the "fuel oil" product may be used to run a diesel engine which is coupled to an electrical generator which supplies power to the electrical heaters on the batch reaction vessel. The steel tire cord which is removed from the thermal processing zone is subsequently cleaned with a liquid in order to remove a heavy hydrocarbon coating, which remains on the surface as an amorphous solid residue, in order to provide for a clean byproduct of steel cord. The light hydrocarbon liquid (the fuel oil) produced in the process has been found to be an excellent cleansing liquid. Alternatively, the liquid heat transfer medium may be used as the cleansing liquid.

The method of the present invention is not limited solely to the reduction of tires into the recovered hydrocarbon products. Any rubber product can be processed. The method of the present invention takes about one hour to process tires into completely separated liquid and solid hydrocarbon products. Radiator hoses, heater hoses, windshield gaskets and other glass/rubber trim products have also been processed in the present invention, and the results have been found to be substantially the same.

Any type of elastomeric product may be processed by the method of the present invention, including natural rubber and synthetic rubber. The synthetic rubbers are generally polymers of open-chained conjugated dienes having from four to eight carbon atoms per molecule, such as, for example, 1,3-butadiene; 2,3-dimethyl-1,3-butadiene; and the like. Examples of such synthetic polymers are polybutadiene, polyisoprene, polychloroprene, styrene-butadiene copolymers, and the like. In general, when discarded automotive vehicle tires are processed, the rubber consists essentially of styrene-butadiene copolymer, although the tire tread will be composed of natural rubber or ethylene-propylene copolymer. Heavy duty tires for trucks, buses and airplanes are typically made of cis-1,4-polyisoprene. In addition, copolymers of mixtures of such conjugated dienes can also be processed, as well as copolymers of monomer systems having a major amount of conjugated diene with a minor amount of a copolymerizable monomer, such as a monomer containing a vinylidene group.

Moreover, any type of polymeric product may be processed by the method of the present invention, regardless whether such product is an elastomeric product. For example, flexible or rigid plastics may be processed by the present invention. Such plastics may include high density and low density polyethylene, polypropylene, polyvinylchloride, polyvinylacetate, polystyrene, polyvinylidenechloride, and the like. Thus, discarded plastic cans, bottles, vials, toys, household utensils, packaging films, and the like may be processed by the method of the present invention. Additionally, electric wiring which is coated with polymeric material may be processed by the method of the present invention to produce hydrocarbons and clean scrap metal.

One type of liquid heat transfer medium which may be utilized for submerging the elastomeric products which are fed into the processing vessel may be an asphalt. The asphalt which may be utilized may include any of the well known bituminous materials such as natural asphalts or those derived from petroleum refining processes such as, for example, vacuum distillation, solvent refining, steam refining with or without air blowing, and the like. When the elastomeric hydrocarbon product of this inventive process is to be utilized in a roofing composition, it is preferred that the asphalt be a roofing asphalt. Such asphalts are typically defined by a softening point by ASTM ring and ball of 90° F. to 240° F. and a penetration at 77° F./100 gm/5 sec. of 10 to 250 dmm. The asphalt is melted within the batch reactor and it functions not only as a liquid heat transfer medium, but also as a solvent, since the elastomeric heavy hydrocarbons which are produced by the thermal cracking of the feed stock elastomeric product readily dissolve in the asphalt.

One particularly preferred type of liquid heat transfer medium which may be utilized for submerging the elastomeric products within the processing vessel may be an aromatic hydrocarbon oil which is sold under the name "SUNDEX 8600T". This product is supplied by Sun Refining And Marketing; Ten Penn Center; Philadelphia, PA. This hydrocarbon liquid heat transfer medium (the aromatic oil) has a predominant number of aromatic ring carbons with a low aniline point which makes it useful as a solvent and a plasticizer. However it does not function as such in the method of the present invention, but it merely functions as a heat transfer liquid. This is indicated by the fact that the amount of heat transfer medium which is added to and removed from the vessel for a batch run remains constant. This aromatic oil is not a residual asphaltic product, but it is a solvent extract which has been scientifically controlled to uniform requirements. It has high viscosity, low volatility, high molecular weight, and a high aromatic content. The aromatics have carbon numbers mainly in the range of C20 through C50. The analysis of a typical aromatic oil of this type shows a molecular weight of about 700 (719) and an aromatic content greater than about 50 Wt.% (typically 57.9 Wt.% aromatics).

FIG. 1 is a simplified schematic representation of a batch reaction vessel 10 which has been used in experimental work for the development of the inventive process. The batch reaction vessel 10 is supported upon a supporting frame 11. The vessel has a cylindrical sidewall 12, a dished head or bottom wall 13, and a top head 14. Within the top head there is located a feed solids loading chamber 16 which has a chamber sidewall 17, a top or outer door or hatch 18, and a bottom or inner door 19 which swings open on hinges (not shown). An inner door control arm or handle 21 for opening and closing the bottom door 19 is supported in the sidewall 17 of the solids loading chamber 16. The handle 21 is attached to the inner door 19 by means of control linkages 22.

A wire basket 24 is contained within the reaction vessel 10 and it sits upon basket supports 25. A liquid level for the heat transfer medium is indicated by the phantom line 26. Contained within the wire basket 24 is an agitator device which consists of an agitator blade 28, and an agitator shaft 29. The shaft 29 passes through a sealing gland 30 in the top head 14 and terminates in a handle 31. This agitator blade is thereby shifted manually in order to stir the contents of the wire basket 24 and agitate the liquid heat transfer medium.

A drain valve 33 is located in the dished head 13 on the bottom of the reaction vessel 10. A vent valve 34 is located in the top head 14 of the reaction vessel. This vent valve is connected to a vent line 35 which functions as an air condenser. The vent line 35 splits into a vapor line 36 for removal of noncondensed hydrocarbon vapor and a liquid line 37 for removal of a light hydrocarbon fraction which has the characteristics of a fuel oil.

As indicated previously, the vessel may be heated by any conventional means. However, it is preferred to heat the vessel by electrical band heaters 39 which are mounted on the outside wall of the vessel 10. Only one surrounding electrical band heater is shown, but a plurality of band heaters may be utilized to the extent that is necessary. A temperature sensing element 40 passes through the cylindrical sidewall 12 of the batch reaction vessel 10. This temperature sensing element 40 may be a dial thermometer, a thermocouple device, or any other suitable temperature sensing and indicating device.

The method of the present invention, as well as the end products produced thereby, may be illustrated by the following Examples.

• EXAMPLE 1

A batch process was operated in an apparatus which was similar to that set forth in FIG. 1, except that facilities were not available for condensing the vapor which was vented out of the top of the vessel. The vessel was loaded with about ten gallons of solid roofing asphalt particles and then heated to a temperature of about 575° F., which is the temperature at which rubber vehicle tires begin to thermally crack. At this point, cut up pieces of vehicle tire were added to the melted asphalt within the vessel. The vessel generated hot vapor which was very smoky. This vapor was vented out of the building. It is believed that the smoke was generated in large part by the thermal cracking of the asphalt. After about an hour, the heating unit, which was a direct fired propane torch on the bottom head 13 of the vessel 10, was shut off and the vessel was allowed to partially cool. Hot liquid asphalt was then withdrawn from the bottom of the vessel. This hot liquid asphalt contained elastomeric hydrocarbons as end products from the thermal cracking of the particles of rubber tire. The elastomeric hydrocarbons remained in solution within the asphalt.

The solution containing the elastomeric hydrocarbons within the roofing asphalt was cooled to produce a solid amorphous material having elastomeric properties and resiliency at room temperature. It did not solidify into the hard, brittle solid which typifies pure asphalt.

This amorphous solid material was exposed to an open flame and it was found to burn readily. However, it was found to be self-extinguishing since it ceased burning upon removal of the flame. In contrast, pure roofing asphalt continued to burn when the flame was removed.

Samples of this asphalt and elastomeric hydrocarbon mixture were placed on square, semi-rigid paperboard sheets having a size of about 1 foot by 1 foot. The sheets containing the elastomeric asphalt mixture coated on the surface were placed out in the sun and leaned at an angle which varied from 45° to 60°. It was determined that the coating of the asphalt with dissolved elastomeric hydrocarbons did not flow at elevated temperatures, such as from 80° to 90° F., in direct sunlight. However, exposure to the elevated temperature and the sunlight caused a control sample of pure roofing asphalt on a 1 foot by 1 foot semi-rigid paperboard card to flow off of the card and onto the ground in the manner of a typical roofing asphalt.

EXAMPLE 2

The solution containing the elastomeric hydrocarbons within the roofing asphalt was applied to a flat roof in a two foot by eight foot test patch. The solution containing the elastomeric hydrocarbons within the roofing asphalt was additionally placed in a two foot by eight foot test patch on a roof having a pitch of 1:2 with a six foot vertical rise on a twelve foot horizontal run (horizontal span).

Both sample patches hardened, but not in a manner similar to that of a conventional pure roofing tar, since the mixture did not become hard and brittle like a normal roofing asphalt on either one of the test patches. Both sample patches formed a skin within one week so that the surface lost its tackiness.

It was found that on warm days (about 90° F. and higher), each patch became soft, but it did not melt and run as a conventional roofing tar alone would have at such temperature conditions. Both sample patches indicated that the content of the elastomeric hydrocarbon within the roofing asphalt imparted resilience to the roofing mixture, because a footprint in the surface of each test strip would disappear within a few hours. It was further determined that on very cold days, such as at a temperature of about 20° F., both test patches became harder, but they still retained their resilience so that a footprint on the surface would eventually disappear after several hours. After the patches had been on the two roofs for about three months, no cracking or other deterioration was observed.

EXAMPLE 3

A batch process was operated in an apparatus as set forth in FIG. 1 except that the apparatus did not have electrical heater bands. Instead, the reaction vessel 10 was heated directly by means of a propane burner located under the bottom head 13. The vessel was charged with 10 gallons of the low volatility, high molecular weight, aromatic hydrocarbon identified hereinabove as SUNDEX 8600T. This aromatic hydrocarbon functioned as the liquid heat transfer medium. It was added to the vessel by pouring it through the solids loading chamber 16. Cut pieces of a single steel belted radial tire were loaded in the solids loading chamber 16. They were dropped into the vessel and submerged in the liquid heat transfer medium after the temperature of the medium had been raised to 575° F. The original tire weighed 33 pounds. The pressure in the vessel 10 was about zero psig as the pieces of tire were cooked in the liquid heat transfer medium. The vessel contents were manually agitated by blade 28 at intervals of about 5 to 10 minutes.

As the pieces of cut tire were cooked in the liquid heat transfer medium in vessel 10, a hot hydrocarbon vapor left the top of the vessel via valve 34 and vent line 35. The vent line 35 functioned as an air condenser. It is apparent to those skilled in the art that a water cooled condenser would have been better placed for this function, but such a device was unavailable at the time that this experiment was run. The cooling which occurred in the vent line 35 was sufficient to cause a light hydrocarbon liquid fraction to leave the apparatus via line 37. At the end of the process run, one quart of this light hydrocarbon fraction was collected. This liquid had the general appearance of a No. 2 fuel oil, but the odor was relatively offensive. As the liquid hydrocarbon left the apparatus via line 37, the uncondensed hydrocarbon vapor passed upwardly via line 36. Because there was no facility available for containing, compressing, and storing this hydrocarbon vapor as it left via line 36, it was burned at the tip of line 36 for purposes of safe disposal. The flame had the characteristic light blue color of a methane-containing hydrocarbon gas.

At the end of 75 minutes, the collection of the light hydrocarbon fraction from line 37 came to an end. This indicated that no further reaction in the processing of the rubber tire pieces would occur under these operating conditions. Accordingly, the unit was shut down and the liquid contents were removed by means of the drain valve 33 in the bottom head 13 of the vessel 10.

The first material removed from the bottom of the vessel was a heavy liquid which contained a gummy solid within it. The liquid was separated from the solid and upon cooling reached the consistency of a grease. This grease-like product is referred to as the light fraction first hydrocarbon solid. Upon cooling, the gummy solid material reached the consistency of a putty. This putty-like material is referred to as the heavy fraction second hydrocarbon solid. After these hydrocarbon materials had been drained from the vessel, the liquid heat transfer medium was removed therefrom. About 10 gallons of the heat transfer medium were collected. This is equivalent to what was added to the vessel at the start of the run. Accordingly, it is concluded that the high molecular weight, low volatility, highly aromatic hydrocarbon liquid does not function as a solvent in the process of this invention, but merely functions as a liquid heat transfer medium.

When the batch vessel had cooled sufficiently for safe removal, the basket 24 was removed from the vessel. The basket was found to contain pieces of steel cord from the tire. Both the pieces of steel cord and the basket itself were coated with a gummy material which was equivalent to the heavy fraction second hydrocarbon solid which was separated from the hot liquid which had been previously removed from the vessel. The basket and the wire cords were shaken sufficiently to remove a substantial portion of the residue contained on the basket and steel cord surfaces. This material was combined with the putty-like material of the heavy fraction second hydrocarbon sold. The material which remained on the basket and the wire cords was washed off by using the light hydrocarbon liquid fraction (the fuel oil) as a cleansing liquid. This hydrocarbon fraction did not dissolve the gummy material as it removed it from the surface of the steel cords and the basket, but merely acted as a cleansing agent. The gummy material settled out from the cleansing agent, and it also was added to the putty-like mass of the heavy fraction second hydrocarbon solid. The light hydrocarbon fraction which had been used as the cleansing liquid contained no contamination from the heavy gummy materials and was placed in storage with the remainder of the light hydrocarbon liquid fraction.

At the end of the run, about one quart of the light fraction hydrocarbon liquid was collected and 3.5 pounds of steel cord was collected. The light fraction first hydrocarbon solid having the consistency of a grease weighed 12 pounds. The heavy fraction second hydrocarbon solid with had the consistency of a putty weighed 16 pounds. The amount of methane-containing gas which was burned at the end of the vent line 36 was not measured since no measuring equipment was available for this purpose.

EXAMPLE 4

Samples of the liquid and solid products produced in the batch operation of Example 3 were sent to a laboratory for Fourier Transform Infrared (FTIR) spectral analysis. The heavy fraction second hydrocarbon solid which had the consistency of putty was found to be composed of high molecular weight hydrocarbons similar to bitumen, which is the highest boiling fraction of crude oils. Thus, the spectrum of this sample was somewhat similar to asphalt. The light fraction first hydrocarbon solid which had the consistency of grease had a spectrum which was similar to that of the heavier putty-like solid except that it contained a considerable amount of other lighter components. They appeared to possibly be oxidized hydrocarbons or hydrocarbon products from thermal cracking of the rubber tire pieces. The light hydrocarbon liquid fraction (the fuel oil) sample was oven "dried" to separate volatiles and non-volatiles. The volatile-free liquid sample was found to be a hydrocarbon mixture which was best matched to a hydrocarbon oil of about 20 Wt.% aromatic content. The more volatile components were found to be a mixture of branched aliphatic and unsaturated aliphatic hydrocarbons.

The light fraction of hydrocarbon liquid, the light fraction first hydrocarbon solid, and the heavy fraction second hydrocarbon solid were tested further. The light fraction hydrocarbon liquid, having the characteristics of a No. 2 fuel oil, was burned in a conventional fuel oil heating nozzle and no unusual observations were made.

The grease-like first hydrocarbon solid was tested by applying heat, and it was determined that this material would melt. In contrast, heat applied to the putty-like second hydrocarbon solid did not cause melting of this putty-like substance. Instead, the heat created smoke and eventually set fire to this putty-like substance.

It was also observed that the grease-like light fraction first hydrocarbon solid was very sticky to the touch, and that the grease-like surface remained soft with time. The putty-like heavy fraction second hydrocarbon solid was less sticky to the touch, and, after several hours, a tacky skin formed on the surface of the putty-like material.

It was further determined that both the grease-like first hydrocarbon solid and the putty-like second hydrocarbon solid could be dissolved in asphalt. This is illustrated by the following Example 5.

EXAMPLE 5

The grease-like first hydrocarbon solid and the putty-like second hydrocarbon solid were each blended with a melted conventional roofing tar (asphalt). Blends of each of the elastomeric solid products in the roofing asphalt were made at intervals of 10 Wt.% in the range of from 10 Wt.% up to 90 Wt.% of the solid products in the roofing asphalt. Sample portions of these blends were placed upon 1 foot by 1 foot square, semi-rigid paperboard sheets for testing.

One set of the sheets for each of the blends for each of the solid products (grease-like and putty-like elastomeric solid products) were put into a conventional food freezer and held there overnight so that the temperature would reach the conventional freezer temperature of about 0° F. ($-17.8°$ C.). On the next morning, the square paperboard samples were removed from the freezer. It was determined that the sample blends of asphalt with the elastomeric solids were not hard and brittle like the control sample of a pure roofing asphalt. The paperboard squares with the blends upon them were bent and flexed. It was determined that flexing the blends of the elastomeric hydrocarbon solids in the asphalt did not cause cracking. This was in contrast to the control sample of pure asphalt which was hard and brittle and did crack when the cardboard backing sheet was flexed. In addition, the cold samples were subjected to a stretching test. Notwithstanding that the samples were cold, those samples of asphalt mixture which contained at least 10 Wt.% of the grease-like first hydrocarbon solid or the putty-like second hydrocarbon solid retained their stretching ability and did not crack.

Equivalent sets of samples of blends at 10 Wt.% intervals were allowed to solidify at room temperature. All sample blends formed amorphous solids having elasticity and resilience. Only a control sample of pure asphalt was hard and brittle. The coated paperboard sample cards were taken outside and exposed to direct sunlight on a warm day when the temperature was in the neighborhood of 90° F. The sample cards were placed on slopes of from 45° to 60°. Under these conditions, a control sample of pure asphalt melted and ran off the card after a period of several hours of exposure to the 90° F. temperature and direct sunlight. In contrast, only those blends containing 10 Wt.% of the grease-like elastomeric solid and the putty-like elastomeric solid in the roofing asphalt melted and ran off of the cards. However, samples containing 60 Wt.% and more of the grease-like elastomeric solid and the putty-like elastomeric solid remained soft without forming a skin, and these samples began to sag so that they may have run off the sample cards if they had been exposed for several days. The other sample blends did not melt and flow off of the card so long as the concentration of the elastomeric solid within the asphalt was from about 20 Wt.% to about 50 Wt.%.

EXAMPLE 6

The grease-like first hydrocarbon solid and the putty-like second hydrocarbon solid were each blended with a conventional roofing tar (asphalt). The blends consisted of 20 Wt.% of the elastomeric solid with 80 Wt.% of the roofing asphalt. Each blend material was applied to a flat roof in a 2 foot by 8 foot test patch.

The blend of the putty-like second hydrocarbon solid with the roofing asphalt hardened, but not in a manner similar to that of a conventional roofing tar, since the mixture did not become hard and brittle like a normal roofing asphalt. The blend of the roofing tar with the grease-like elastomeric solid also solidified, but it never achieved a hardness like the blend of the putty-like second hydrocarbon solid with the roofing tar. Both blends formed a skin within one week so that the surface lost its tackiness.

It was found that on warm days (about 90° F. and higher), the patch which contained the grease-like elastomeric solid became very soft, but it did not melt and run as a conventional roofing tar alone would have at such temperature conditions. On the other hand, the blend of the putty-like elastomeric solid with the roofing tar did not become appreciably softer at the same temperature.

Both sample patches indicated that addition of the grease-like and putty-like solids imparted resilience to the roofing mixture, because a footprint in the surface of the test strip would disappear within a few hours. It was further determined that on very cold days, such as at a temperature of about 20° F., both test patches became harder but they still retained their resilience so that a footprint on the surface would eventually disappear after several hours. After the patches had been on the roof for about three months, no cracking or other deterioration was observed.

It is to be understood that the foregoing examples are given for illustrative purposes only. Although the method was tested in a batch process, those skilled in the art of process design can readily provide a continuous processing system for practicing the method of the present invention.

The mechanism under which the inventive method operates is not clearly understood. However, it is apparent from the generation of methane-containing gas and fuel oil that thermal cracking of the elastomeric polymer (the rubber products) is occurring. Whether or not thermal cracking of the SUNDEX 8600T liquid heat transfer medium occurs is not known. However, it is generally known that hydrocarbon cracking does not occur until temperatures of from about 680° F. to about 700° F. are experienced. It is also known that aromatic hydrocarbons are the most difficult to crack. Since the method of the present invention operates at temperatures below this level, and since the SUNDEX 8600T liquid heat transfer medium is 57.9 Wt.% aromatics, it is believed that thermal cracking of only the rubber products occurs and that little or no cracking of this heat transfer liquid is occurring. This seems to be confirmed by the fact that the amount of this heat transfer liquid remaining at the end of a batch run is equal to what was charged into the vessel to begin the run.

Operating conditions for the inventive method may be varied in accordance with the specific liquid heat transfer medium which is utilized in the thermal processing zone (the vessel). The time may be for a period of from about 0.5 hour to about 2 hours, although it is preferred that the operation be conducted for a period sufficient to generate the ultimate amount of the fuel oil liquid. As seen in Example 3, this period was 1.25 hours for a steel belted radial tire weighing 33 pounds. When the heat transfer medium is the highly aromatic hydrocarbon oil utilized in Example 3, it is preferred that the temperature be maintained at about 575° F., although the temperature has been as high as 600° F. with no problem occurring. However, it has been determined that thermal cracking of rubber tires does not occur at temperatures below about 575° F. The pressure within the thermal processing zone will generally be a nominal zero psig if the generated vapor is vented to the atmosphere as illustrated in Example 3.

In Example 6, the elastomeric hydrocarbon grease-like and putty-like solid products were used with asphalt as a roofing composition. Alternatively, these elastomeric hydrocarbon solids may be mixed with pavement grade asphalt and the mixture may be used for highway construction and pavement maintenance. Additionally, these elastomeric hydrocarbon solids may have other uses, such as in adhesive compositions and sealants. Similarly, the light hydrocarbon liquid fraction is not limited to use as a fuel oil or diesel oil. Depending upon its composition, it may have other uses. For example, in those instances where this product has a high aromatic content, it may have utility as a high octane blending component for automotive gasoline.

In light of the foregoing disclosure, further alternative embodiments of the inventive method will undoubtedly suggest themselves to those skilled in the art. It is thus intended that the disclosure be taken an illustrative only, and that it not be construed in any limiting sense. Other modifications and variations may be resorted to without departing from the spirit and the scope of this invention, and such modifications and variations are considered to be within the purview and the scope of the appended claims.

The inventions claimed:

1. Method for the recovery of hydrocarbon from elastomeric products which comprises:
   a.) passing elastomeric products selected from the group consisting of products of natural rubber and products of synthetic rubber into a substantially air-free thermal processing zone;
   b.) contacting said elastomeric products in said thermal processing zone with a low volatility liquid heat transfer medium comprising a high molecular weight hydrocarbon liquid;
   c.) maintaining said thermal processing zone under elevated temperature conditions sufficient to generate a first hydrocarbon vapor from the elastomeric products within said processing zone;
   d.) passing said first hydrocarbon vapor from said thermal processing zone into a condensation zone;
   e.) recovering from said condensation zone a second hydrocarbon vapor containing light hydrocarbons selected from the group consisting of hydrocarbons having one, two, three, four and five carbon atoms per molecule and mixtures thereof;
   f.) recovering from said condensation zone a light fraction first hydrocarbon liquid comprising hydrocarbons having more than five carbon atoms per molecule;
   g.) recovering a light fraction elastomeric first hydrocarbon solid from said processing zone; and, h.) recovering a heavy fraction elastomeric second hydrocarbon solid from said processing zone.

2. Method according to claim 1 wherein a heavy fraction second hydrocarbon liquid is withdrawn from said processing zone at an elevated temperature, at least a portion of said elastomeric second hydrocarbon solid is settled out of said second hydrocarbon liquid to produce a third hydrocarbon liquid, and said third hydrocarbon liquid is cooled to provide said elastomeric first hydrocarbon solid.

3. Method according to claim 1 wherein said heat transfer medium comprises a high molecular weight hydrocarbon liquid having a high aromatic content.

4. Method according to claim 3 wherein said hydrocarbon liquid has a molecular weight of about 700 and an aromatic content greater than about 50 Wt.%.

5. Method according to claim 1 wherein said elevated temperature conditions include a temperature at least in the range of from about 575° F. to about 600° F.

6. Method according to claim 5 wherein said elevated temperature conditions include a time period of from about 0.5 hours to about 2.0 hours.

7. Method according to claim 5 wherein said elevated temperature conditions are maintained until recovery of said first hydrocarbon liquid ceases to occur.

8. Method according to claim 7 wherein said recovery of said first hydrocarbon liquid ceases to occur after about 1.25 hours.

9. Method according to claim 1 wherein said elevated temperature conditions are maintained until recovery of said first hydrocarbon liquid ceases to occur.

10. Method according to claim 9 wherein said recovery of said first hydrocarbon liquid ceases to occur after about 1.25 hours.

11. Method according to claim wherein said elevated temperature conditions include a time period of from about 0.5 hours to about 2.0 hours.

12. Method according to claim 1 wherein said first hydrocarbon liquid comprises aromatic hydrocarbons.

13. Method according to claim 12 wherein said first hydrocarbon liquid contains an aromatic content of about 20 Wt.%, as indicated by FTIR spectral analysis.

14. Method according to claim wherein said first hydrocarbon liquid contains volatile components comprising a mixture of branched aliphatic and unsaturated aliphatic hydrocarbons, as indicated by FTIR spectral analysis.

15. Method according to claim wherein said first hydrocarbon liquid has properties of a hydrocarbon fuel oil.

16. Method according to claim 1 wherein said elastomeric first hydrocarbon solid comprises high molecular weight hydrocarbons similar to bitumen and lighter hydrocarbons, as indicated by FTIR spectral analysis.

17. Method according to claim 16 wherein said lighter hydrocarbons comprise oxidized hydrocarbons, as indicated by FTIR spectral analysis.

18. Method according to claim 1 wherein said elastomeric first hydrocarbon solid has the consistency of a grease.

19. Method according to claim 18 wherein said elastomeric first hydrocarbon solid is sticky.

20. Method according to claim 1 wherein said elastomeric second hydrocarbon solid comprises high molecular weight hydrocarbons similar to bitumen, as indicated by FTIR spectral analysis.

21. Method according to claim 1 wherein said elastomeric second hydrocarbon solid has the consistency of putty.

22. Method according to claim 21 wherein said elastomeric second hydrocarbon solid has the surface property of a tacky skin.

23. Method according to claim wherein said elastomeric products comprise vehicle tires and steel cord is recovered from said processing zone.

24. Method according to claim 23 wherein said recovered steel cord is coated with a third hydrocarbon solid, and said third hydrocarbon solid is cleaned from said steel cord by a cleaning liquid to provide a substantially hydrocarbon-free steel cord product and a mixture of said third hydrocarbon solid in said cleaning liquid.

25. Method according to claim 24 wherein said third hydrocarbon solid is separated from said cleaning liquid and is combined with said recovered elastomeric second hydrocarbon solid, and said cleaning liquid is thereby rendered substantially free of said third hydrocarbon solid.

26. Method according to claim 24 wherein said cleaning liquid comprises a portion of said first hydrocarbon liquid.

27. Method according to claim 24 wherein said cleaning liquid comprises a portion of said liquid heat transfer medium.

28. Method according to claim 1 performed as a batch process.

29. Method according to claim 1 performed as a continuous process.

30. Method for the recovery of hydrocarbons from elastomeric products which comprises:
    a.) passing elastomeric products selected from the group consisting of products of natural rubber and products of synthetic rubber into a substantially air-free thermal processing zone;
    b.) contacting said elastomeric products in said thermal processing zone with a low volatility liquid heat transfer medium comprising a high molecular weight hydrocarbon;
    c.) maintaining said thermal processing zone under elevated temperature conditions sufficient to generate a first hydrocarbon vapor from the elastomeric products within said processing zone;
    d.) passing said first hydrocarbon vapor from said thermal processing zone into a condensation zone;
    e.) recovering from said condensation zone a second hydrocarbon vapor containing light hydrocarbons selected from the group consisting of hydrocarbons having one, two, three, four and five carbon atoms per molecule and mixtures thereof;
    f.) recovering from said condensation zone a light fraction first hydrocarbon liquid comprising hydrocarbons having more than five carbon atoms per molecule;
    g.) withdrawing a heavy fraction second hydrocarbon liquid comprising thermally cracked elastomeric hydrocarbons and liquid heat transfer medium from said thermal processing zone; and,
    h.) cooling said second hydrocarbon liquid to provide a recovered elastomeric solid product comprising said thermally cracked elastomeric hydrocarbons and heat transfer medium.

31. Method according to claim 30 wherein said low volatility liquid heat transfer medium comprises melted asphalt.

32. Method according to claim 31 wherein said asphalt is a roofing grade asphalt.

33. Method according to claim 30 wherein said elevated temperature conditions include a temperature at least in the range of from about 575° F. to about 600° F.

34. Method according to claim 33 wherein said elevated temperature conditions include a time period of from about 0.5 hours to about 2.0 hours.

35. Method according to claim 33 wherein said elevated temperature conditions are maintained until recovery of said first hydrocarbon liquid ceases to occur.

36. Method according to claim 35 wherein said recovery of said first hydrocarbon liquid ceases to occur after about 1.25 hours.

37. Method according to claim 30 wherein said elevated temperature conditions are maintained until recovery of said first hydrocarbon liquid ceases to occur.

38. Method according to claim 37 wherein said recovery of said first hydrocarbon liquid ceases to occur after about 1.25 hours.

39. Method according to claim 30 wherein said elevated temperature conditions include a time period of from about 0.5 hours to about 2.0 hours.

40. Method according to claim 30, wherein said first hydrocarbon liquid comprises aromatic hydrocarbons.

41. Method according to claim 40 wherein said first hydrocarbon liquid contains an aromatic content of about 20 Wt.%, as indicated by FTIR spectral analysis.

42. Method according to claim 30 wherein said first hydrocarbon liquid contains volatile components comprising a mixture of branched aliphatic and unsaturated aliphatic hydrocarbons, as indicated by FTIR spectral analysis.

43. Method according to claim 30 wherein said first hydrocarbon liquid has properties of a hydrocarbon fuel oil.

44. Method according to claim 30 wherein said elastomeric products comprise vehicle tires and steel cord is recovered from said processing zone.

45. Method according to claim 30 performed as a batch process.

46. Method according to claim 30 performed as a continuous process.

* * * * *